United States Patent [19]
Chang et al.

[11] Patent Number: 5,753,823
[45] Date of Patent: May 19, 1998

[54] RUBBER SUBSTRATE SHEAR LAP-JOINT TESTING FIXTURE

[75] Inventors: Dick J. Chang, Los Angeles; William D. Hanna, Rolling Hills Estates, both of Calif.

[73] Assignee: The Aerospace Corporation, El Segundo, Calif.

[21] Appl. No.: 884,614

[22] Filed: Jun. 27, 1997

Related U.S. Application Data

[62] Division of Ser. No. 609,409, Mar. 1, 1996, Pat. No. 5,705,752.

[51] Int. Cl.$^6$ ................................................. G01N 3/24
[52] U.S. Cl. ........................ 73/842; 73/845; 73/827
[58] Field of Search ........................... 73/826, 827, 834, 73/838, 841, 842, 845, 846

[56] References Cited

U.S. PATENT DOCUMENTS

| | | | |
|---|---|---|---|
| 4,346,609 | 8/1982 | Gould et al. | 73/842 |
| 4,541,286 | 9/1985 | Roper | 73/827 |
| 4,957,004 | 9/1990 | McKinlay | 73/842 |
| 5,176,028 | 1/1993 | Humphrey | 73/842 |
| 5,537,884 | 7/1996 | Nishimura et al. | 73/842 |
| 5,705,752 | 1/1998 | Chang et al. | 73/827 |

Primary Examiner—George M. Dombroske
Assistant Examiner—Max H. Noori
Attorney, Agent, or Firm—Derrick Michael Reid

[57] ABSTRACT

A back-to-back, single lap-joint test fixture and method provides for uniform shear strength determination in a lap-joint area at an adhesive bond plane between a low-modulus rubber-like elastic material substrate and a stiff panel both defining a single lap-joint specimen, two of which are disposed back-to-back with the rubber substrates being constrained from lateral deformation by respective aluminum housings each having a load-transferring lip pushing upon a substrate also being pulled by load transferring dowel pins pulling upon the rubber substrate while with a restraining clamp that restrains transverse movement of the housing and rubber substrate all so as to produce only shear-type failures based on the near-incompressible nature of the rubber materials in the two back-to-back single lap-joint specimens.

3 Claims, 2 Drawing Sheets

Back-to-Back Lap Joint Test Fixture

Back-to-Back Lap Joint Test Fixture

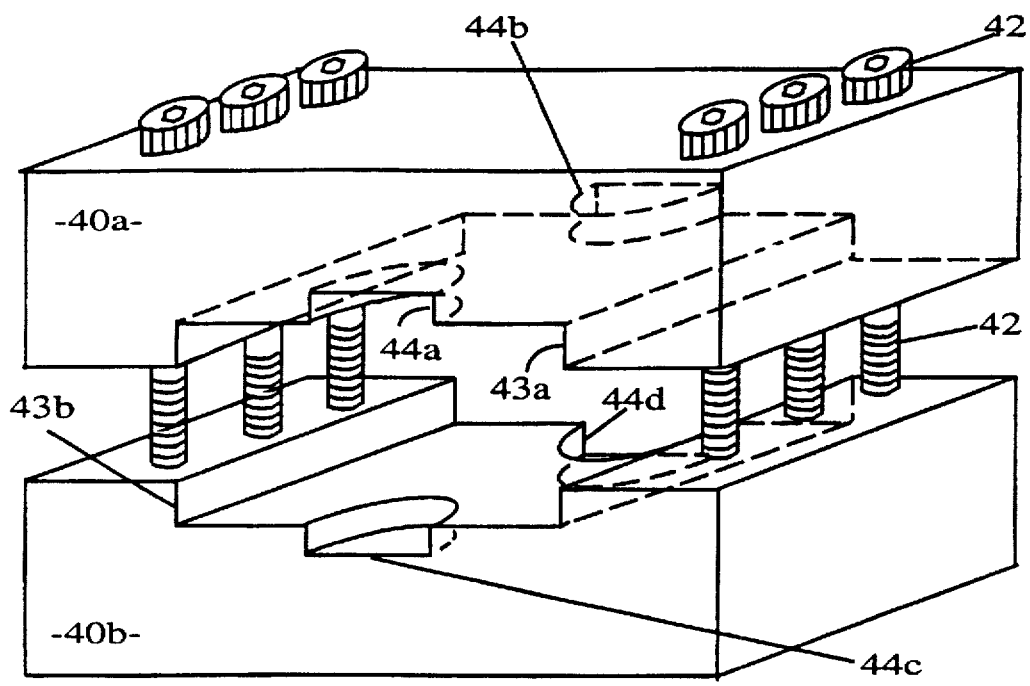
Restraining Clamp  FIG. 2
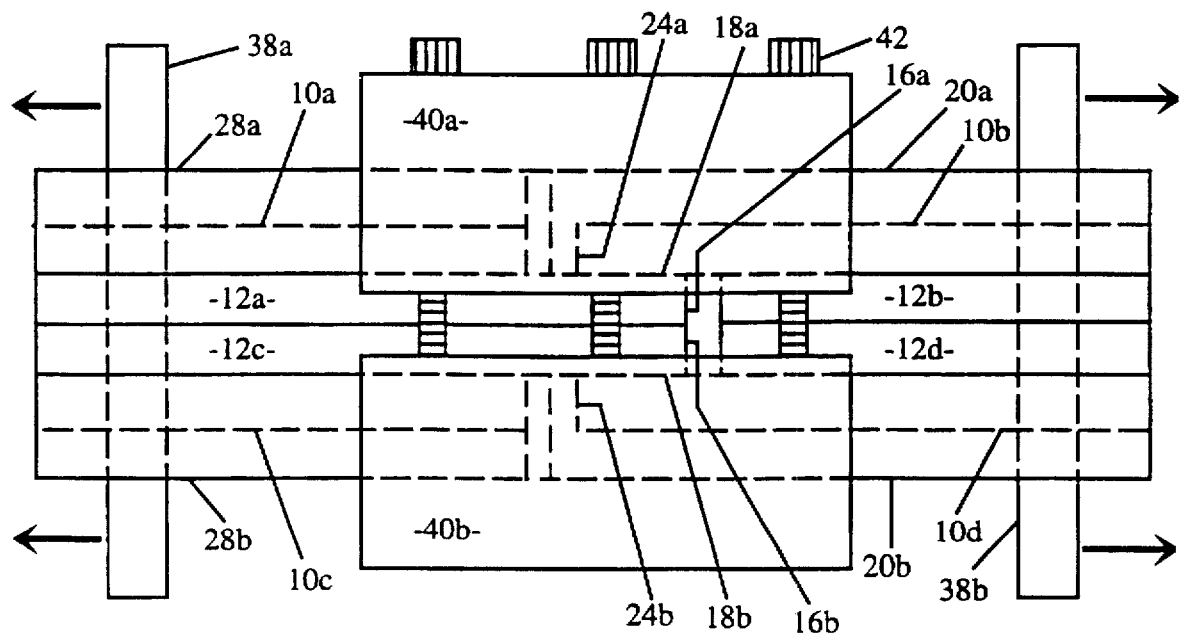
Test Assembly  FIG. 3

RUBBER SUBSTRATE SHEAR LAP-JOINT TESTING FIXTURE

REFERENCE TO RELATED APPLICATION

This application is a divisional of application Ser. No. 08/609,409 filed Mar. 1, 1996, now U.S. Pat. No. 5,705,752. +gi

STATEMENT OF GOVERNMENT INTEREST

The invention was made with Government support under Contract No. F04701-88-C-0089 by the Department of the Air Force. The Government has certain rights in the invention.

The invention described herein may be manufactured and used by and for the government of the United States for governmental purpose without payment of royalty therefor.

SPECIFICATION

FIELD OF THE INVENTION

The present invention relates to the field of bond strength testing. More specifically, the present invention related to shear testing of adhesive bond strength on low-modulus rubber-like elastic materials.

BACKGROUND OF THE INVENTION

Rubber substrate laminated upon a supporting panel are used as thermal insulators, structural supports and shock resistance coverings, among many other uses. For example, ethylene propylene diene monomer (EPDM) rubber substrates and carbon phenolic panels have been used on critical motors in space rocket engines. A debond between these two components due to operating stresses may cause failure of entire systems. A determination of the shear bond strength between the rubber substrate and the panel is important.

Determining shear strength of the adhesive bond between the rubber substrate and the panel is difficult because the generation of pure shear in mechanical testing is a very challenging task. Single and double lap-joint shear tests have been accepted as standard methods to determine shear strength of adhesive materials. It is well known, however, that stress singularities exist at the ends of adherents for both types of testing. In addition, cleavage tension stress singularities exist in single lap-joints.

When one of the substrates of a lap-joint is made from low modulus material such as rubber, the failure is no longer in shear mode. Rather, the failure is dominated by tension because very large deformation occurs in the rubber, causing the rubber to peel away from the joint. Consequently, the joint fails in bulk tension inside the low modulus substrate material. It is desired to have a uniform test method for generating shear-type failures for shear lap-joint specimens with rubber substrates. Test data is needed to assess the structural integrity of structures ranging from a wide variety of assembled components. For instance, when using composite materials with multiple layers of laminae, the adhesive strength data become increasingly important.

There are problems in determining the material tension and shear bond strengths for a given adhesive on a substrate material using laboratory testing in common practice. While the tensile testing is relatively simple, the shear strength testing is more difficult. Shear bond testing tests shear bond strength at the substrate-panel interface. A problem resides in the fact that the pure shear stress testing is very difficult to design, and a uniform pure shear testing design is nearly impossible to achieve. The failure mode in conventional shear lap-joint tests with rubber-like substrates is predominantly tensile peeling. This is primarily caused by very large deformation of the rubber substrate as a result of load application. Because of the low modulus, most of the load transmission between the rubber substrate and the adhesive occurs at the tip of the interface of these two materials, which induces tensile failure.

For a substrate of rubber-like material of which the elastic modulus is very low, i.e., the material is very compliant and is easy to deform under force, the shear strength testing for the adhesive bond to a panel becomes more difficult. All the lap-shear test standards specified by The American Society for Testing and Materials (ASTM) are generally not suitable for a very low modulus rubber-like elastic substrate bonded to a panel because of the high tensile stress associated with the large deformation of the low modulus rubber substrate.

Low modulus rubber-like elastic materials are known to be nearly incompressible. "Incompressibility" is a term used herein to describe the attribute that a constant volume is preserved while the material is being deformed under force. Technically, compressibility is used to describe how easily the volume of a given material can be compressed under the application of a uniform pressure. The bulk modulus of a material is defined as the ratio of the applied pressure, P, to the material volume change ratio, $dV/V$, where V is the material volume under ambient pressure and dV is the change in volume from the ambient pressure to the applied pressure. When the bulk modulus $M=P/|dV/V|$ is low, the compressibility is large, and the material is considered compressible. It is known that low-modulus rubber-like elastic material becomes nearly incompressible when restrained from deforming. Lap-joint shear testing fixtures and methods have failed to adequately shear test unconstrained rubber-like elastic material, and as a result, unconstrained rubber-like elastic material substrate exhibit tension failures at bonded substrate-panel interfaces.

There is no suitable existing test method known for shear-type failure testing of a shear lap-joint specimen having a low modulus, rubber-like substrate. There is no standard test method to measure adhesive shear strength for this type of structure. All known conventional test methods fail to generate valid results for adhesive joints with rubber-like substrates. These and other disadvantages are solved or reduced using the present invention.

SUMMARY OF THE INVENTION

An object of this invention is to provide a shear bond testing method and fixture of elastic materials.

Another object of this invention is to provide shear bond testing method and fixture of elastic materials that become nearly incompressible when restrained.

Yet another object of the present invention is to provide a shear bond testing method and fixture of low modulus elastic rubber-like substrate.

Still another object of the invention is to provide shear bond testing of elastic substrate using lap fixtures and longitudinal pulling load.

A further object of the present invention is to provide shear bond testing of back-to-back lap fixtures of elastic substrates bonded to respective panels in laterally restrained and vertically clamped test assemblies.

Still a further object of the present invention is to determine the adhesive-substrate bonding shear strength.

A restrained substrate, made of a low-modulus rubber-like elastic material is bonded to a panel in a lap-joint configuration for adhesive bond shear strength testing of the substrate to panel bonded interface. The restrained rubber-like elastic material is nearly incompressible so that failure of the bond interface results from only shear stresses. ASTM standards for lap-shear testing of low-modulus substrates can now be uniformly performed over a large range of low modulus rubber-like elastic materials. The term shear strength used herein can be bulk shear strength of an adhesive material itself or the interfacial shear strength between the adhesive and either of the two adherents.

The test configuration includes a single lap-joint specimen of the substantially horizontal flat rectangular left-to-right elongated substrate bonded by an adhesive to a like shaped panel. A substrate groove is preferably cut widthwise across and through the substrate down to the adhesive thereby separating the substrate into a left substrate portion and a right substrate portion. Another but parallel panel groove is similarly cut widthwise across and through the panel up to the adhesive thereby separating the panel into a left panel portion and right panel portion. The depth of the recessed substrate groove is made equal to the thickness of the substrate. The depth of the recessed panel groove is made equal to the thickness of the panel. Between the substrate groove and the panel groove is defined a cross sectional horizontal bond line between the substrate and panel. The shear test bonded area, or lap-joint, is the horizontal bonded area of substrate and panel between these two vertically extending grooves. A housing, which is preferably a metal, such as aluminum, is fitted tightly on the outside of the right substrate portion on four outer surfaces, the top surface, the front edge and the two edge sides. The housed substrate becomes a restrained rubber-like elastic material. The rubber-like elastic substrate now has higher stiffness than that of the unrestrained rubber-like material so that failure would result from only shear tension. During testing, a longitudinal pulling force is applied to the lap-joint specimen to simultaneously pull the right portions away from the left portions, so as to apply only shearing forces along the bonded shear test area, that is, through the joint. In the preferred form of the invention, brackets, which are also preferably made of metal, such as aluminum, are fitted tightly on the outside of the left portion of substrate on three outer surfaces, the top surface, and the two edge sides.

The pulling force is preferably applied through dowel pins. A right dowel pin passes through the housing and right portions while a left dowel pin passes through the bracket and left portions. The pulling force is used to uniformly measure the bond shear strength on the bonded shear test area. Preferably, a bolt passes through housing and right portions and another bolt passes through the bracket and left portions to transfer part of an applied load from the housing to the rubber, thus creating a pulling action to the joint at the bond shear test area from both sides of the bond shear test area. The balance of the applied load is transmitted to the shear test substrate portion through front edge of the housing as a pushing action upon the front edge of the substrate as part of the shear load. The bolts and dowel pins provide vertical alignment during testing.

In the preferred form of the invention, a text fixture of two identical horizontally disposed single lap-joint specimens are positioned back-to-back with the substrate grooves in vertical alignment and with the panel groove also is vertical alignment so that the two like bond shear test areas, that is the lap-joints, are also in vertical alignment. The two single lap-joint specimens are placed back-to-back so that the outer surface of the two panels buttress each other. The area between the grooves along the bond line plane represents the joint area receiving shear test loading when the pulling force is applied equally to both specimens through the same dowel pins. The back-to-back specimens may further be clamped together by a restraining clamp to enhance uniform application of the pulling force. The external restraining clamp is used to clamp the test fixture. The restraining clamp may be made of heavy steel and used to restrain the transverse movement of the housing and transverse (vertical) deformation of the substrates. The clamp should buttress the housings initially without applying any substantial transverse force. The back-to-back bracketed, bolted and clamped lap shear fixture is the preferred test assembly to provide uniform bond shear testing. After the lap shear fixture and restraining clamp are assembled together as a test assembly, the longitudinal pulling load is applied to the two specimens through the dowel pins at a desired load or displacement rate. The specimens will finally fail through shear forces in the shear loaded area, that is, along the lap-joints.

In summary, the invention relies upon the near incompressibility of the rubber-like materials. Restraint of rubber deformation using the housing and clamp makes the rubber substrate exceedingly stiff and nearly incompressible. Consequently, a large deformation of the rubber-like substrate does not occur. The shear load is applied through both pulling and pushing to the rubber-substrate to generate only shear forces in the lap-joint. The loading action distributes the load to the shear loaded area in a more uniform fashion and results in more constant shear stress distribution.

The test method determines the shear strength in the lap-joint of rubber-like material used as a substrate. The design of the test fixture takes advantage of the near-incompressible nature of the rubber material. The test fixture includes a stiffened aluminum restraining housing with a load-transferring front edge flange pushing on the front end of the rubber substrate. The housing is combined with the restraining clamp that restrains transverse deformation of the substrate within the test assembly. The preferred test method uses a test fixture that produces shear-type failures on two back-to-back single lap-joint specimens. The test method is a viable technique in determining shear strength of bond line of a rubber-like material used as a substrate.

The present invention is applicable to all polymeric materials that are incompressible in nature. The shear bond strength of a given adhesive on any polymer can be determined using the test fixtures and methods described herein. These and other advantages will become more apparent from the following detailed description of the preferred embodiment.

BRIEF DESCRIPTION OF THE DRAWINGS

FIG. 2 is a drawing of a restraining clamp.

FIG. 3 is a drawing of a test assembly.

DETAILED DESCRIPTION OF THE PREFERRED EMBODIMENT

Figure 1:
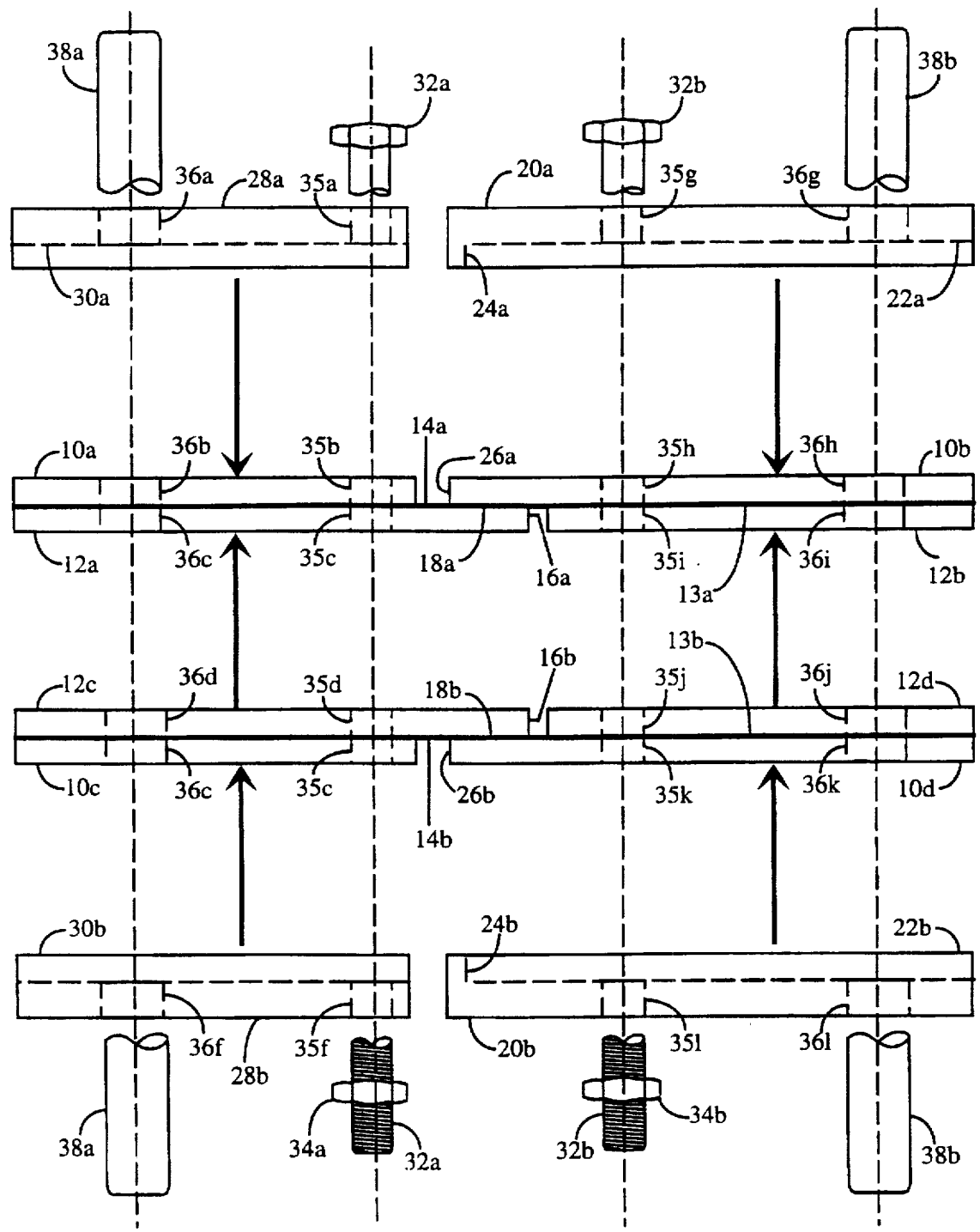
FIG. 1 is a drawing of a back-to-back single lap-joint test fixture.

An embodiment of the present invention is described with reference to the figures using reference designations as shown in the figures. Referring to FIG. 1, which shows a back-to-back single lap-joint shear test fixture, a first substantially horizontal flat rectangular left-to-right elongated substrate having left portion 10a and right portion 10b and a second similarly shaped substrate having a left portion 10c and a right portion 10d are respectively bonded to a first panel having a left portion 12a and a right portion 12b and a second panel having a left portion 12c and a right portion 12d. Top substrate portions 10ab are bonded by an adhesive layer 13a to top panel portions 12ab and bottom substrate portions 10cd are bonded by another adhesive layer 13b to bottom panel portions 12cd. The substrate portions 10a and 10b, and 10c and 10d are also referred to as substrates 10ab and 10cd both also referred to as substrates 10, and portions 12a and 12b, and 12c and 12d are also referred to as panels 12ab and 12cd both also referred to as panels 12. The substrates 10 may be made of a low-modulus rubber-like elastic material and the panels 12 are made of a hard bondable material.

The substrates 10ab and 10cd are bonded by to like shaped panels 12ab and 12cd. Substrate grooves 14a and 14b are preferably cut widthwise across and through the substrates 10ab and 10cd respectively separating portions 10a and 10b, and 10c and 10d, respectively. The grooves 14a and 14b extend, respectively, through the substrates 10ab and 10cd to the respective adhesive layers 13a and 13b, respectively, thereby separating the substrates 10ab and 10cd into respective left and right substrate portions 10a and 10b, and 10c and 10d, respectively. Parallel panel grooves 16a and 16b are similarly cut widthwise across and through the panels 12ab and 12cd to the respective adhesive layers 13a and 13b, respectively, separating the panels 12ab and 12cd into portions 12a and 12b, and 12c and 12d, respectively. The depth of the recessed substrate grooves 14 is made equal to the thickness of the substrates 10. The depth of the recessed panel grooves 16 is made equal to the thickness of the panels 12. Substrate portions 10abcd and panel portions 12abcd have the same width while portion pairs 10a and 10c, 10b and 10d, 12a and 12c, and 12b and 12d have the same length. Portions 10a, 10b, 10c and 10d have the same thickness. Portions 12a, 12b, 12c and 12d have the same thickness.

Between substrate grooves 14a and the panel groove 16a is defined a cross sectional horizontal lap-joint 18a between the right substrate portion 10b and left panel portion 12a. Between substrate grooves 14b and the panel groove 16b is defined a cross sectional horizontal lap-joint 18b between the right substrate portion 10ad and left panel portion 12c. The shear test bonded area, that is, the lap-joint 18a or 18b, is a horizontal bonded area of respective substrate right portion 10b or 10d along respective adhesive layer 13a or 13b over a respective area of right panel portion 12b or 12d, respectively, between the two vertically extending grooves 14a and 16a, or 14b and 16b. Alternatively, grooves 14 and 16 may be formed by bonding pre-cut respective portions 10abcd and 12abcd bonded together as shown and having gaps defining the grooves 14 and 16.

A top housing 20a and a bottom housing 20b, which are preferably metal, such as aluminum, have respective housing cavities 22a and 22b both adapted to be fitted tightly on the outside of respective right substrate portions 10b and 10d. The depth of the recessed cavities 22ab is made equal to the thickness of the substrates 10. The housings 20a and 20b have respective front flanges 24a and 24b which buttress respective front edges 26a and 26b of the right substrate portions 10b and 10d, respectively. Of similar width and height to the housing, brackets 28a and 28b, which are also preferably metal, such as aluminum, have respective bracket cavities 30a and 30b both adapted to be fitted tightly on the outside of left substrate portions 10a and 10c. The brackets 28a and 28b have the same length as the respective left substrate portions 10a and 10c. The brackets 28a and 28b and housings 20a and 20b all have the same width.

For the lap-joint test fixture assembly, designated by arrows, the substrates 10, panels 12, housings 20 and brackets 28 are joined together using bolts 32a and 32b and nuts 34a and 34b. During assembly, the top panels portions 12a and 12b respectively buttress bottom panel portions 12c and 12d, the brackets 28a and 28b respectively fit on left substrate portions 10a and 10c, and housings 20a and 20b respectively fit on substrate portions 10b and 10d. During assembly, the left bolt 32a passes through aligned left bolt apertures 35a, 35b, 35c, 35d, 35e and 35f in the top bracket 28a, top left substrate portion 10a, top left panel portion 12a, bottom left panel portion 12c, bottom left substrate portion 10c, and bottom bracket 28b, respectively, as the right bolt 32b passes through aligned right bolt apertures 35g, 35h, 35i, 35j, 35k and 35l in the top housing 20a, top right substrate portion 10b, top right panel portion 12b, bottom right panel portion 12d, bottom right substrate portion 10d, and bottom housing 20b, respectively. The nuts 34a and 34b are respectively screwed tightly onto bolts 32a and 32b during assembly causing grooves 14a and 14b to assemble in vertical alignment and causing grooves 16a and 16b to assemble in vertical alignment, so that, lap-joints 18a and 18b are also assembled in vertical alignment. During screwing assembly, apertures 36a, 36b, 36c, 36d, 36e and 36f respectively through the top bracket 28a, top left substrate portion 10a, top left panel portion 12a, bottom left panel portion 12c, bottom left substrate portion 10c, and bottom bracket 28b, assemble together in vertical alignment, as apertures 36g, 36h, 36i, 36j, 36k and 36l respectively through the top housing 20a, top right substrate portion 10b, top right panel portion 12b, bottom right panel portion 12d, bottom right substrate portion 10d, and bottom housing 20b, also assembled together in vertical alignment. After assembly, the apertures 36a–f are in vertical alignment and adapted to receive a left dowel pin 38a while apertures 36g–l are in vertical alignment and adapted to receive a right dowel pin 38b.

Referring to FIGS. 1 and 2, and particularly to FIG. 2, a restraining clamp has two parts, a top part 40a and a bottom part 40b clamped together by a plurality of Allen wrench clamp bolts 42, only one of which is shown designated. Each of the clamp bolts pass through the top part 40a and are screwed into the bottom part 40b. The clamp bolts 42 are used to clamp together parts 40a and 40b in vertical alignment. Each of the parts 40a and 40b respectively include a vertically aligned rectangular apertures 43a and 43a respectively extending longitudinally left-to-right the length of the parts 40a and 40b. At proximal (left) and distal (right) ends of the aperture 43a are respectively disposed semicircular cavities 44a and 44b. At proximal (left) and distal (right) ends of the aperture 43b are respectively disposed semicircular cavities 44c and 44d.

Referring to all of the Figures, the assembled back-to-back lap-joint test fixture of FIG. 1 is disposed between restraining clamp parts 40a and 40b. The ends of left bolt 32a are received into semicircular cavities 44a and 44c while the ends of right bolt 32b are received into semicircular cavities 44b and 44d. The screws 42 are turned to clamp the parts 40a and 40b around the test fixture including bolts 34, brackets 28a and 28b, housings 20a and 20b substrates portions 10a, 10b, 10c and 10d, panel portions 12a, 12b, 12c and 12d. The restraining clamp of FIG. 2 is shown in FIG. 3 restraining the back-to-back lap joint test fixture of FIG. 1. In FIG. 3, the bolts 32, nuts 34, cavities 44, and apertures 35 are not shown for simplicity. The restraining clamp of part 40a and 40b clamp upon the test fixture components 10, 12, 20 and 28 having extending dowel pins 38 resulting in a combined test assembly.

The housed right substrate portions 10bd become respectively restrained within the housings 20ab when respectively fitted over the right substrate portions 10bd. The low modulus rubber-like elastic substrate has higher stiffness now than when unrestrained so that failure results from only shear tension. In the preferred form of the invention, two identical horizontally disposed single lap-joint specimens each having a substrate 10 and a bonded panel 12, are positioned back-to-back in vertical alignment so that the two like bond shear test areas 18a and 18b, that is the lap-joints, are also in vertical alignment. The two single lap-joint specimens 10ab–12ab, and 10cd–12cd, are placed back-to-back so that the outer surface of the two panels 12ab and 12cd buttress each other in configured symmetry to maximize uniformity during shear testing. The area between the grooves 14 and 16 along the bond line 13 represents the joint area 18 receiving shear test loading when the pulling force is applied equally to both through the dowel pins 38. The back-to-back specimens are then clamped together by a restraining clamp 40ab to enhance uniform application of the pulling force. The external restraining clamp 40ab is used to clamp the lap fixture. The restraining clamp 40ab is preferably made of heavy steel. The restraining clamp 40ab serves to restrain the transverse (vertical) deformation of the substrate portions 10bd which causes transverse movement of the housings 20ab. The clamp 40 should buttress the housing 20 without initially applying any substantial transverse compressive force orthogonal to the longitudinally extending substrate 10. The back-to-back lap-joint shear fixture of FIG. 1 becomes a preferred test assembly when bolted and clamped to provide uniform bond shear testing.

A longitudinal pulling force is applied to the lap-joint 18ab by simultaneously pulling the right portions 10bd–12bd away from the left portions 10ac–12ac, so as to apply only shear tension along the bonded shear test area 18ab, that is, through the lap-joint 18ab. The pulling force is preferably applied through the dowel pins 38. The right dowel pin 38b passes through the housings 20ab and right portions 10bd and 12bd while the left dowel pin 38a passes through brackets 28ab and left portions 10ac and 12ac. The pulling force on the dowel pins 38 is used to uniformly measure the bond shear strength on the bonded shear test area 18ab. The bolts 32a and 32b which respective pass through brackets 28ab and housings 20ab, left substrate portions 10ac and right substrate portions 10bd, and, left panel portions 12ac and right panel portions 12bd transfer part of an applied load on the pins 38ab through the bolts 32ab creating a pulling action upon the lap-joints at the bond shear test area 18ab from both left and right sides. The balance of the applied load on the pins 38ab is transmitted to the right substrate portions 10bd through front edges 24ab of respective housings 20ab as a pushing action upon the front edge 26ab of the right substrate portions 10bd as part of the shear load on the lap-joints 18ab. After all the lap shear fixture components 10, 12, 20 and 28 and restraining clamp 40 are mounted together as a test assembly, the longitudinal pulling load is applied to the joints 18ab through the dowel pins 38ab with any desired load or displacement rate. The joints 18ab will finally fail through shear tension.

Without the restraining clamp 40ab, the rubber substrate 10bd deforms and pushes the aluminum housing 20ab away from the substrate 10bd such that the substrate front edge 26ab and housing flange 24ab are no longer in contact with each other. No contact between front edge 26ab of the substrate 10bd and the tip 24a of the aluminum housing 20ab means that no more load is transmitted from the housing 20ab to substrate 10bd through pushing action. The clamp 40ab provides the restraint necessary to ensure that the specimens 10ab–12ab and 10cd–12cd, brackets 28ab and housings 20ab work monolithically as one integral piece. When the boundary surfaces of the rubber substrate 10bd are constrained from transverse movement, the rubber substrate 10bd becomes very stiff because of its near incompressibility. Restraining the vertical movement of rubber substrates 10bd eliminates the peeling type of failure in the rubber substrates and thereby leads to more uniform shear stress along the rubber substrate adhesive interface of the lap-joint 18ab. Transversely induced forces in the rubber substrates during the test are high during testing. The restraining clamp 40ab prevents the transverse rubber deformation. Constraining the substrate portions 10bd by the housings 20ab prevents lateral deformation of the substrate portions 10bd orthogonal to the transverse deformation.

The rubber substrate 10 is stiffened by the housing 20 that redistributes load transfer more uniformly so that shear type failure will prevail. This is done by transferring the applied load from a stiffened panel 12 to the rubber substrate 10 partly through pulling from one end and partly through pushing at the other end. This simultaneous application of pushing and pulling of the rubber substrate will result a much smaller longitudinal deformation in the rubber and a more uniform force transmission at the substrate and the adhesive interface. The specimens 10ab–12ab and 10cd–12cd used in the test method are lap-joint configurations which are easy to fabricate and can be widely used in shear tests.

Suitable panels 12 are fabricated by the various suppliers, such as Thiokol Corporation. In this particular case, FM 5064 graphite-reinforced phenolic (carbon phenolic) panels have a layer of rubber bonded to only one side, but two single lap-joint specimens can be tested simultaneously in a back-to-back configuration with a transverse restraining clamp so that the combined specimens behave like a double-joint specimen. The preferred test configuration consists of a stiff phenolic panel and a soft rubber substrate, for examples. Phenolic panels and nitride butadiene rubber (NBR) substrates, and WC8 harness satin fabric FM 5064 carbon phenolic panels and ethylene propylene diene monomer (EPDM) rubber substrates. The panel and substrate are bonded together using a strong adhesive, such as Epon EA 934 NA adhesive applied as a bond layer 13. The bonded substrates 10 and panels 12 may be vacuum bagged and cured at 325° F. The curing pressure may be 150 psi for 5 hr.

EPDM bonded carbon phenolic composite panels specimens may be machined finished into pairs of specimens so as to obtain nearly identically shaped bonded specimens 10 and 12. The pairs of specimens 10 and 12 with brackets 28 and housings 20 may then have holes 35 and 36 drilled for near perfect alignment and then be finished so as to obtain aligned assembled back-to-back lap-joint test fixtures.

False high failure loads may be attributed to a high compression on the aluminum bracket 28 and housing 20 from the clamping action when the clamp 40ab is over-tightened. The clamp 40ab should be applied to the joint 18ab so that no initial transverse compression normal to the surface of the rubber substrate is induced. That is, the contact between the housing 20 and bracket 28 to the clamp 40ab should be snug but preferably not tight because the load at shear failure of the joint. 18 would be increased by any transverse compression normal to the rubber substrate surface. When the clamp 40ab is tightly compressed against the rubber substrate 10, the load causing shear failure may increase significantly compared with the snug condition. The snug condition closely corresponds to actual shear failure.

Specimens dimensions may be, for example, 15.2 cm long by 2.3 cm wide. The thicknesses of the phenolic panel 12 and NBR substrate 10 may be 0.32 cm and 0.38 cm, respectively. The thickness of the Epon EA 934 NA adhesive is preferably between 0.01 to 0.04 cm between the substrate 10 and panel 12. The transverse grooves 14 and 16 are machined from both the phenolic panel side 12 and the rubber substrate side 10, both to the epoxy interface therebetween to create the shear lap-joints 18. In modified test procedures, the grooves 14 and 16 may extend into the adhesive interface 18, while for others test procedures, the grooves 14 and 16 extend only to the adhesive interfaces 18. Because the adhesive fails at very low strain level, the impact of the cutting into the adhesive is insignificant.

Shear testing may be conducted using a conventional pulling tester, such as an Instron Universal testing machine, model 1127. Typical speed of the loading crosshead may be 0.51 cm/min. Applied load vs. crosshead displacement for each specimen should be recorded. Each specimen should be visually inspected during and after completion of the testing. The length of the lap-joints 18a between the grooves 14 and 16 may be, for examples, between 0.762 to 2.290 cm. Too long of a lap-joint 18 may not evenly distribute the load therethrough. The best uniform shear-type failures occur when the joints 18ab are not longer than 1.524 cm, and preferably not longer than 1.270 cm. A longer lap-joint 18ab tends to have uneven shear stress over the area of the lap-joint 18ab. A lap-joint 18ab shorter than 0.762 cm may have large edge effects. Hence, an optimal lap-joint 18ab should be between 0.762 and 1.270 cm long. For a 0.762 cm lap-joint length, the shear strength varies from 4.09 to 4.97 MPa, with an average of 4.46 MPa for the specimens prepared. For both 1.020 and 1.270 cm lap-joint lengths, the measured strengths are about twenty five percent lower than the 0.762 cm lap-joint length. The failure loads have good uniformity between various specimens of the same materials and dimensions. Shear failure modes are either interfacial shear-type debond between the adhesive 13 and the adherents 10 and 12, while others are cohesive shear failures within the adhesive 13 in the lap-joint 18.

Linear and elastic finite element stress analysis for a lap-joint may help determine the stress distributions under various prescribed boundary conditions. The results of the analysis may provide useful information in arriving at optimal specimen configuration and may identify test fixture refinements. A basic finite element model may be used for a plane strain configuration in the width direction. Such a model may consists of an 0.46 cm thick aluminum bracket, a 0.32 cm thick carbon phenolic panel, a 0.38 cm thick rubber substrate, and an adhesive layer of 0.013 cm of thick Epon EA 934 NA adhesive. The parameters varied in the analysis include the length of the lap-joints 18ab, the width of the grooves 14 and 16, the width of the lip of the aluminum bracket 28 and housing 20, and loading transfer upon the substrate to adhesive interface which has a strong influence on the stress concentration at the tip 24ab of the joint 18. The length of lap-joints 18ab, the width of the grooves 14 and 16, and the width of aluminum lip 24ab should be varied during analysis. The stresses in the lap-joints 18ab are induced by a longitudinal displacement of the right end relative to the left end. The displacement value may be arbitrary since the purpose of the analysis is to determine an optimal specimen configuration for uniform shear stress distribution along the bond line 13 within the test area 18 rather than the actual magnitudes of the stresses. Transverse displacements at the carbon phenolic side are constrained to simulate the symmetrical boundary conditions in the actual testing. The output includes the nodal displacements, and the element stresses and strains in longitudinal-length, transverse-thickness and lateral-width directions.

Analyzed lap-joint length of 0.762 cm has relatively even load distribution but has high stress concentration at the tip 26ab. The 1.270 cm long lap-joint length has very uniform shear stress distribution. Analysis also indicates that longitudinal lap-joint lengths between 0.762 and 1.270 cm are preferred. The width of the transverse substrate groove 14 may have an effect on the stress concentration at the tip 26ab. A wide groove 14 tends to allow more chance for stress redistribution, and thus reduce the stress concentration. A 0.318 cm wide groove 14 cutting through the adhesive layer 13 is optimal.

Another important variable is the transverse length of the housing front flange 24ab. The length of the flange 24a may be as long the transverse depth of the groove 14ab which is typically the thickness of the rubber substrate 10abcd. The analytical results suggest that there is a high stress concentration at the front edge 26ab of the rubber substrate 10bd the near the bond line 13 within test area 18ab. With a downwardly or upwardly extending flange length 24ab shorter than the thickness of the substrate 10abcd, the load from the housing 20ab transfers gradually through the rubber substrate 10bd to the bond line 18ab, thereby inducing smaller stress concentration. There preferably is a very small free space gap, not shown, which may be greater than the thickness of the adhesive layer 13ab, and preferably about twice the thickness of the adhesive layer 13ab, between the bottom of the substrate groove 14ab and the end of the front housing flange 24ab. For example, with a substrate 10abcd thickness of 0.38 cm and an adhesive layer of 0.013 cm, the length of the front flange 24ab may have a length 0.356 cm with a gap of 0.026 cm. Thus, linear elastic finite element analyses may be used to assist in the optimization of test parameters.

Specimen geometry parameters and load application fixture designs may improve the shear stress distributions in the lap shear joints for improved uniform testing. Test specimens machined from carbon phenolic panels, Epon EA 934 NA adhesive, and EPDM substrates had an average failure stresses of 4.46, 3.39, and 3.32 MPa for the 0.762, 1.016, and 1.270 cm long lap-joints 18ab, respectively. Some of the failures were initiated inside the adhesive 13 of the lap-joint 18 whereas other failures occurred between the adhesive 13 of the lap-joint 18 and the substrate 10. The shear failures loading result are relatively uniformed.

Those skilled in the art may make modifications, enhancements and improvements to the forgoing test fixtures and assemblies which may be based upon using empirical data or computer aided analysis. However, those enhancements, improvements and modifications may nonetheless fall within the spirit and scope of the following claims.

What is claimed is:

1. A method for testing the shear strength of a top lap-joint under stress from an external load, the method comprises the steps of bonding a top substrate to a top panel using an adhesive along a top bond plane, cutting a top substrate groove into the top substrate forming top left and top right substrate portions, cutting a top panel groove into the top panel to form top left and top right panel portions, the top lap-joint defined as the top bond plane between the top substrate groove and the top panel groove, constraining the top substrate portion to resist lateral deformation to isolate shear tension in the top lap-joint during testing, and, transferring the external load to the top lap-joint.

2. The method of claim 1 wherein the transferring step concurrently applies the external load to both the top lap-joint and a bottom lap-joint, the method is for concurrently testing the bottom lap-joint and the top lap-joint, the method further comprises the steps of, bonding a bottom substrate to a bottom panel using an adhesive along a bottom bond plane, cutting a bottom substrate groove into the bottom substrate forming bottom left and bottom right substrate portions, cutting a bottom panel groove into the bottom panel to form bottom left and bottom right panel portions, the bottom lap-joint defined as the bottom bond plane between the bottom substrate groove and the bottom panel groove, constraining the bottom substrate portion to resist lateral deformation to isolate shear tension in the bottom lap-joint during testing, aligning back-to-back the top panel portions against the bottom panel portions to align the top and bottom lap-joints, and restraining transverse deformation of the top substrate and bottom substrate portions to isolate shear tension in the top and bottom lap-joints during testing.

3. The method of claim 2 further comprising the steps of fastening together the right substrate portions and right panel portions in vertical alignment, and fastening together the left substrate portions and left panel portions in vertical alignment.

* * * * *